United States Patent [19]

Brüning et al.

[11] Patent Number: 4,988,526
[45] Date of Patent: Jan. 29, 1991

[54] HEMIMERCAPTALS, PROCESSES FOR THEIR PREPARATION, AND EDIBLE COMPOSITIONS CONTAINING SAME

[75] Inventors: Jürgen Brüning; Roland Emberger; Matthias Güntert; Rudolf Hopp; Manfred Köpsel; Theodor Sand, all of Holzminden; Peter Werkhoff, Hoexter, all of Fed. Rep. of Germany

[73] Assignee: Haarmann & Reimer GmbH, Holzminden, Fed. Rep. of Germany

[21] Appl. No.: 406,481

[22] Filed: Sep. 13, 1989

[30] Foreign Application Priority Data

Sep. 21, 1988 [DE] Fed. Rep. of Germany ....... 3831981

[51] Int. Cl.$^5$ ................................................. A23L 2/26
[52] U.S. Cl. ..................................... 426/535; 549/66; 549/479
[58] Field of Search .................. 426/535; 549/66, 479

[56] References Cited

U.S. PATENT DOCUMENTS 4,031,256 6/1977 Evers et al. ....................... 426/535
4,477,678 10/1984 van den Bosch et al. .......... 426/535

OTHER PUBLICATIONS

A. Streitwieser et al., "Introduction to Organic Chemistry", 1976, MacMillan Pub. Co., pp. 242-243, 1214-1215.

Primary Examiner—Donald E. Czaja
Assistant Examiner—Anthony Weier
Attorney, Agent, or Firm—Sprung Horn Kramer & Woods

[57] ABSTRACT

New hemimercaptals of the formula

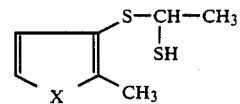

in which
X represents an oxygen or sulphur atom, a process for their preparation and their use as flavorings have been found.

6 Claims, No Drawings

HEMIMERCAPTALS, PROCESSES FOR THEIR PREPARATION, AND EDIBLE COMPOSITIONS CONTAINING SAME

The invention relates to new hemimercaptals, a process for their preparation and their use as flavourings.

New hemimercaptals of the formula

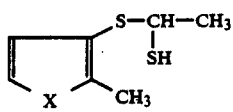

in which
X represents an oxygen or sulphur atom,
have been found which have useful organoleptic properties.

The hemimercaptals of the formula (I) according to the invention are obtained by condensation of thiols of the formula

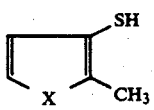

in which
X has the meaning indicated under formula (I), with acetaldehyde and treatment of the compounds formed in the condensation of the formula

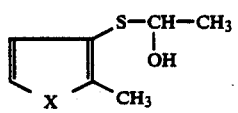

in which
X has the meaning indicated under formula (I), with hydrogen sulphide.

The invention therefore also relates to a process for the preparation of hemimercaptals of the formula (I), which is characterized in that thiols of the formula (II) are condensed with acetaldehyde in the presence of hydrogen sulphide in aqueous solution at temperatures from 0° C. to 10° C. in the presence of an organic acid, preferably acetic acid. Both process steps, condensation and conversion of the hydroxyl group of the condensation product into the SH group, can be combined to give a one-step reaction combination, in which the condensation is immediately carried out in the presence of hydrogen sulphide.

The thiols of the formula (II) required as starting compounds are known (see DE-OS (German Published Specification) 2,458,609).

The compounds according to the invention are useful flavourings which are distinguished by very low taste threshold values. The taste descriptions read:
1-(2-methyl-3-furylthio)ethanethiol: roasty, meaty, broth, vegetable
1-(2-methyl-3-thienylthio)ethanethiol: broth, meaty, pork, sulphury, yeasty As a result of their specific taste tending towards meat, the compounds of the formula (I) according to the invention have a taste-strengthening and rounding-off effect in meat flavour compositions. However, the compounds according to the invention also cause a rounding-off of the flavour and an increase in the fullness of taste in other flavour compositions, for example nut flavours.

This flavour compositions prepared using the compounds according to the invention can be employed in the entire foodstuffs and luxury food area, and also in animal feed. In particular, they are suitable for fat mixtures, bakery products, extruded products, ready-to-serve meals, meat and sausage products, soups, sauces, preserved vegetables and all types of industrially prepared animal feed.

The new hemimercaptals according to the invention are used in amounts of 5 ppt to 1%, preferably 100 ppt to 100 ppm, relative to the foodstuff ready for consumption.

The percentage data used in the examples are in % by weight.

EXAMPLE 1

30 ml of methylene chloride and 0.5 ml of acetic acid are added to a solution of 4 g (0.1 mol) of sodium hydroxide in 36 ml of water saturated at 0° C. with hydrogen sulphide. 4.4 g (0.1 mol) of acetaldehyde and 13 g (0.1 mol) of 2-methyl-3-thienylthiol are added dropwise to the mixture with stirring. The pH of the reaction mixture is kept at 5 to 6 by the addition of about 10 g of acetic acid. During the dropwise addition and the subsequent reaction at room temperature for 2 hours, hydrogen sulphide is introduced in order to maintain the saturation of the solution by hydrogen sulphide. After keeping at room temperature for 12 hours, the reaction mixture is rendered alkaline by addition of sodium hydroxide and the organic phase is separated off and discarded. The aqueous phase is acidified with dilute hydrochloric acid and extracted with ether. The combined ether extracts are worked up in a customary manner. 3 g of crude product are obtained; these yield 0.3 g of 1-(2-methyl-3-thienylthio)ethanethiol after distillation at 71° C./0.3 mbar.

A sample of the compound purified by preparative gas chromatography was identified by its IR, NMR and mass spectra.

EXAMPLE 2

The procedure was as described in Example 1, only an equivalent amount (0.1 mol) of 2-methyl-3-furylthiol was employed instead of 2-methyl-3-thienylthiol.

0.5 g of 1-(2-methyl-3-furylthio)ethanethiol was obtained. A sample of the compound purified by preparative gas chromatography was identified by its IR, NMR and mass spectra.

EXAMPLE 3

A meat flavour composition is prepared by mixing the following constituents:

| | |
|---|---|
| 50:50 mixture of Na inosinate and Na guanilate | 1 |
| Monosodium glutamate | 19 |
| Lactic acid, spray-dried | 30 |
| Vegetable protein hydrolysate (type RFB of the FIS) | 350 |
| Sweet whey powder | 100 |
| Edible salt | 500 |
| | 1000 |

A 1% strength aqueous solution of this composition is used as a control sample.

If 500 ppt of 1-(2-methyl-3-furylthio)ethanethiol are added to the control sample, the taste of the aqueous solution of a test group is described as considerably more meaty in comparison to the control sample. The same effect is achieved by the addition of 2 ppb of 1-(2-methyl-3-thienylthio)ethanethiol to the control sample.

What is claimed is:

1. A hemimercaptal of the formula

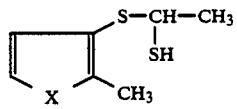
(I)

in which

X is oxygen or sulphur.

2. A process for the preparation of a hemimercaptal of the formula

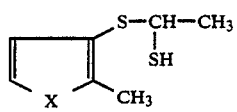
(I)

in which

X is oxygen or sulphur, which process comprises condensing a thiol of the formula

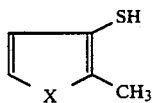
(II)

in which

X has the meaning indicated under formula (I), with acetaldehyde in the presence of $H_2S$.

3. A process for strengthening the taste and rounding off the flavour of a flavour composition which comprises adding to the flavour composition an amount of the hemimercaptal of claim 1 sufficient to flavour the composition.

4. An edible composition comprising a foodstuff and an amount of the hemimercaptal of claim 1, sufficient to flavour the composition.

5. The edible composition of claim 4 comprising a foodstuff and 0.000005 to 1% of the hemimercaptal relative to the foodstuff ready for consumption.

6. A hemimercaptal according to claim 1 in which X is sulphur.

* * * * *